(12) United States Patent
Fosaaen et al.

(10) Patent No.: US 8,851,933 B2
(45) Date of Patent: Oct. 7, 2014

(54) RELEASABLE ELECTRICAL CONNECTION

(71) Applicant: Kerdea Technologies, Inc., Greenville, NC (US)

(72) Inventors: Ken Ervin Fosaaen, Winterville, NC (US); Robert Louis Bartosh, Attleboro, MA (US)

(73) Assignee: Kerdea Technologies, Inc., Greenville, NC (US)

( * ) Notice: Subject to any disclaimer, the term of this patent is extended or adjusted under 35 U.S.C. 154(b) by 0 days.

(21) Appl. No.: 13/792,468

(22) Filed: Mar. 11, 2013

(65) Prior Publication Data
US 2014/0256194 A1     Sep. 11, 2014

(51) Int. Cl.
*H01R 24/00*     (2011.01)
*H01R 4/48*      (2006.01)

(52) U.S. Cl.
CPC .................................. *H01R 4/4818* (2013.01)
USPC ........................................................ 439/660

(58) Field of Classification Search
USPC ............... 439/660, 699.1, 913, 350, 930, 656
See application file for complete search history.

(56) References Cited

U.S. PATENT DOCUMENTS

| | | | |
|---|---|---|---|
| 2,075,019 A | 3/1937 | Buck et al. | |
| 2,385,915 A | 10/1945 | Hagedorn et al. | |
| 3,247,315 A | 4/1966 | Miller | |
| 3,366,915 A * | 1/1968 | Miller | 439/295 |
| 3,452,315 A | 6/1969 | Deakin | |
| 3,631,373 A | 12/1971 | Matrisian | |
| 3,831,133 A * | 8/1974 | Grundfest | 439/680 |
| 4,203,648 A | 5/1980 | Seidler | |
| 4,284,487 A | 8/1981 | Barnes et al. | |
| 4,302,067 A | 11/1981 | Monson et al. | |
| 4,395,081 A | 7/1983 | Melys | |
| 4,502,745 A | 3/1985 | Chavers et al. | |
| 4,565,001 A * | 1/1986 | Patton | 29/866 |
| 4,738,627 A | 4/1988 | Seidler | |
| 4,897,055 A * | 1/1990 | Jurista et al. | 439/699.1 |
| 4,900,279 A | 2/1990 | Dennis | |
| 4,902,251 A * | 2/1990 | Grzena | 439/699.2 |
| 4,991,666 A | 2/1991 | Septfons et al. | |
| 5,000,702 A * | 3/1991 | Forish et al. | 439/699.2 |
| 5,051,108 A | 9/1991 | Lincoln | |
| 5,120,233 A * | 6/1992 | Mikola | 439/356 |
| 5,238,414 A * | 8/1993 | Yaegashi et al. | 439/108 |
| 5,329,806 A | 7/1994 | McClanahan et al. | |
| 5,490,788 A | 2/1996 | Mazzochette | |
| 5,573,650 A | 11/1996 | Fukaya et al. | |
| 5,807,147 A | 9/1998 | Bickford | |
| 5,977,860 A | 11/1999 | Ulm, Jr. et al. | |
| 6,010,369 A * | 1/2000 | Itabashi et al. | 439/660 |
| 6,146,166 A | 11/2000 | Muzslay | |
| 6,261,136 B1 | 7/2001 | Dennis | |
| 6,867,504 B2 | 3/2005 | Lichtenwalter et al. | |

(Continued)

FOREIGN PATENT DOCUMENTS

EP          1 544 609 A1      6/2005
JP       2012 230076 A       11/2012

*Primary Examiner* — Phuong Dinh
(74) *Attorney, Agent, or Firm* — Coats & Bennett, PLLC

(57) ABSTRACT

A releasable electrical connection and related methods use lateral compression of an electrically conductive spring to form a forced abutting solderless connection between the spring and a corresponding electrical lead, with the lead pressed between the spring and a support. The connection can be readily broken and remade for servicing related electrical equipment, such as an oxygen sensor assembly.

20 Claims, 9 Drawing Sheets

(56) References Cited

U.S. PATENT DOCUMENTS

| | | |
|---|---|---|
| 7,410,364 B2 * | 8/2008 | Kishi et al. ............... 439/74 |
| 7,931,509 B2 | 4/2011 | Shaw et al. |
| 8,313,336 B2 * | 11/2012 | Bondo et al. ............... 439/324 |
| 2011/0186446 A1 | 8/2011 | Fosaaen |
| 2012/0214357 A1 | 8/2012 | Flaherty, IV |

* cited by examiner

RELEASABLE ELECTRICAL CONNECTION

BACKGROUND

The present invention relates to electrical connections, and more particularly to releasable electrical connections.

Numerous approaches have been taken for making electrical connections. For example, some electrical connections are made by soldering wires together. However, such connections are not readily releasable. As such, numerous releasable connection approaches have been proposed, such as the USB connector found in numerous electronic devices for power and/or data transmission. However, USB and similar connections may not be suitable for some applications, such as in harsh environments. As such, there remains a need for alternative approaches to making releasable electrical connections.

SUMMARY

A releasable electrical connection is described that relies on lateral compression of an electrically conductive spring, which may be generally cylindrical, to form a forced abutting connection between the spring and a corresponding electrical lead, with the lead pressed between the spring and a support.

In one or more embodiments, a releasable electrical connector assembly includes a cap portion and a base portion. The cap portion is releasably mated to the base portion such that the cap portion and the base portion longitudinally overlap. The cap portion includes an electrically non-conductive cap outwardly laterally bounding a cavity. The cap portion also includes a first electrical conductor assembly extending through the cap and partially disposed in the cavity. The first electrical conductor assembly includes a first conductor and a spring mounted to a distal end portion of the first conductor. The spring extends along a longitudinal spring axis and has a circumference about the spring axis. The base portion includes a core extending proximally toward the cap and an electrically conductive lead disposed outward of the core. The spring is laterally compressed between the cap and the lead such that, at a first longitudinal location along the spring axis, a first portion of the circumference of the spring is non-conductively abutting the cap and a second portion of the circumference, disposed at the first longitudinal location along the spring axis, is electrically conductively abutting the lead. The lead, at the first location, directly faces the core on a side of the lead opposite the spring.

The base portion may be proximally enclosed by the cap. The spring may comprise a coil having multiple layers disposed in convolute fashion about the spring axis. There are advantageously additional pairs of leads and conductor assemblies that are spaced from each other around the core axis, advantageously substantially similar to the first lead and conductor assembly. The various additional pairs may be disposed symmetrically relative to the core. The second portion of the circumference may subtend an angle of not more than about 10° about the spring axis. In some embodiments, the base portion includes an oxygen sensor electrically coupled to the lead.

In one or more embodiments, a releasable electrical connector assembly includes a female cap portion releasably mated to a male base portion such that the cap portion and the base portion longitudinally overlap. The female cap portion includes an electrically non-conductive cap outwardly laterally bounding a first cavity;

a first electrical conductor assembly extending through the cap and having an distal end portion disposed in the cavity; the first electrical conductor assembly including a first conductor and a first spring mounted to a distal end portion of the first conductor. The spring extends distally along a longitudinal first spring axis. The male base portion includes a non-conductive core extending proximally toward the cap along a longitudinal core axis and having an outer surface disposed about the core axis. The male portion also includes a first electrically conductive lead disposed outward of the outer surface of the core. The core and the first lead are disposed in the cap so that: 1) proximate the cavity the first lead is pressed between the outer surface of the core and the first spring; 2) the spring is laterally compressed normal to the first spring axis between the first lead and the cap; 3) an electrical path extends between the first conductor and the first lead via the first spring. In some embodiments, the electrical connector assembly may include one or more additional cavities, springs, leads disposed so as to form additional electrical connections.

In one or more embodiments, a method of electrical connection includes providing a cap portion and a base portion. The cap portion includes an electrically non-conductive cap bounding a cavity. The cap portion further includes a first electrical conductor assembly extending through the cap and having an end portion disposed in the cavity. The first electrical conductor assembly includes a first conductor and a spring mounted to a distal end portion of the first conductor. The spring extends along a longitudinal spring axis and having a peripheral external surface disposed about the spring axis. The base portion includes a core extending proximally along a longitudinal base axis toward the cap, and an electrically conductive lead disposed outward of the core. The method includes moving the cap portion distally and relative to the base portion and to engagement therewith so as to releasably mate the cap portion to the base portion such that the cap portion and the base portion longitudinally overlap. The releasably mating causes lateral compression of the spring between the cap and the lead such that a first portion of the external surface of the spring non-conductively abuts the cap and a second portion of the external surface, disposed at a same longitudinal location along the spring axis as the first portion, electrically conductively abuts the lead to electrically connect the first conductor to the lead.

In some embodiments, the releasably mating includes proximally enclosing the base portion with the cap portion. The method may further include crimping the spring to the end portion of the first conductor. The cap portion may further include a shell disposed outwardly from the cap, and the releasably mating may include releasably engaging the shell with the base portion. The method may include removing a first base portion from the cap portion so as to break an electrical connection between the conductor associated therewith and the first lead. Thereafter, a second base portion is releasably coupled to the cap portion such that the cap portion and the second base portion longitudinally overlap. As a result of coupling the cap portion to the second base portion, the spring is laterally compressed between the cap and the second lead of the second base portion such that a third portion of the external surface of the spring non-conductively abuts the cap and a fourth portion of the external surface, disposed at a same longitudinal location along the spring axis as the third portion, electrically conductively abuts the second lead to electrically connect the first conductor to the second lead.

In one or more embodiments, a method of electrical connection includes releasably mating a female cap portion to a male base portion such that the cap portion and the base portion longitudinally overlap. The female cap portion includes an electrically non-conductive cap, having a cavity, and a first electrical conductor assembly. The first electrical conductor assembly extends through the cap and has an distal end portion disposed in the cavity. The first electrical conductor assembly includes a first conductor and a first spring mounted to a distal end portion of the first conductor, with the spring extending distally along a longitudinal first spring axis. The male base portion includes a nonconductive core extending proximally toward the cap along a longitudinal core axis, with an outer surface disposed about the core axis. A first electrically conductive lead is disposed outward of the outer surface of the core. The mating includes moving the female cap portion distally toward the male base portion such that: 1) the core enters an opening of the female cap; 2) the first lead is pressed inward between the outer surface of the core and the first spring; 3) the spring is laterally compressed normal to the first spring axis between the first lead and the cap; 4) an electrical path is formed between the first conductor and the first lead via the first spring.

The various aspects discussed above may be used alone or in any combination. Further, the present invention is not limited to the above features and advantages. Indeed, those skilled in the art will recognize additional features and advantages upon reading the following detailed description, and upon viewing the accompanying drawings.

DETAILED DESCRIPTION

The present application is directed to a releaseable electrical connector and/or methods of making releasable electrical connections. The discussion below may generally be in the context of a releasable electrical connection for a combustion engine oxygen sensor assembly, but it should be understood that the releasable electrical connection(s) disclosed herein may be used in other applications.

Figure 1:
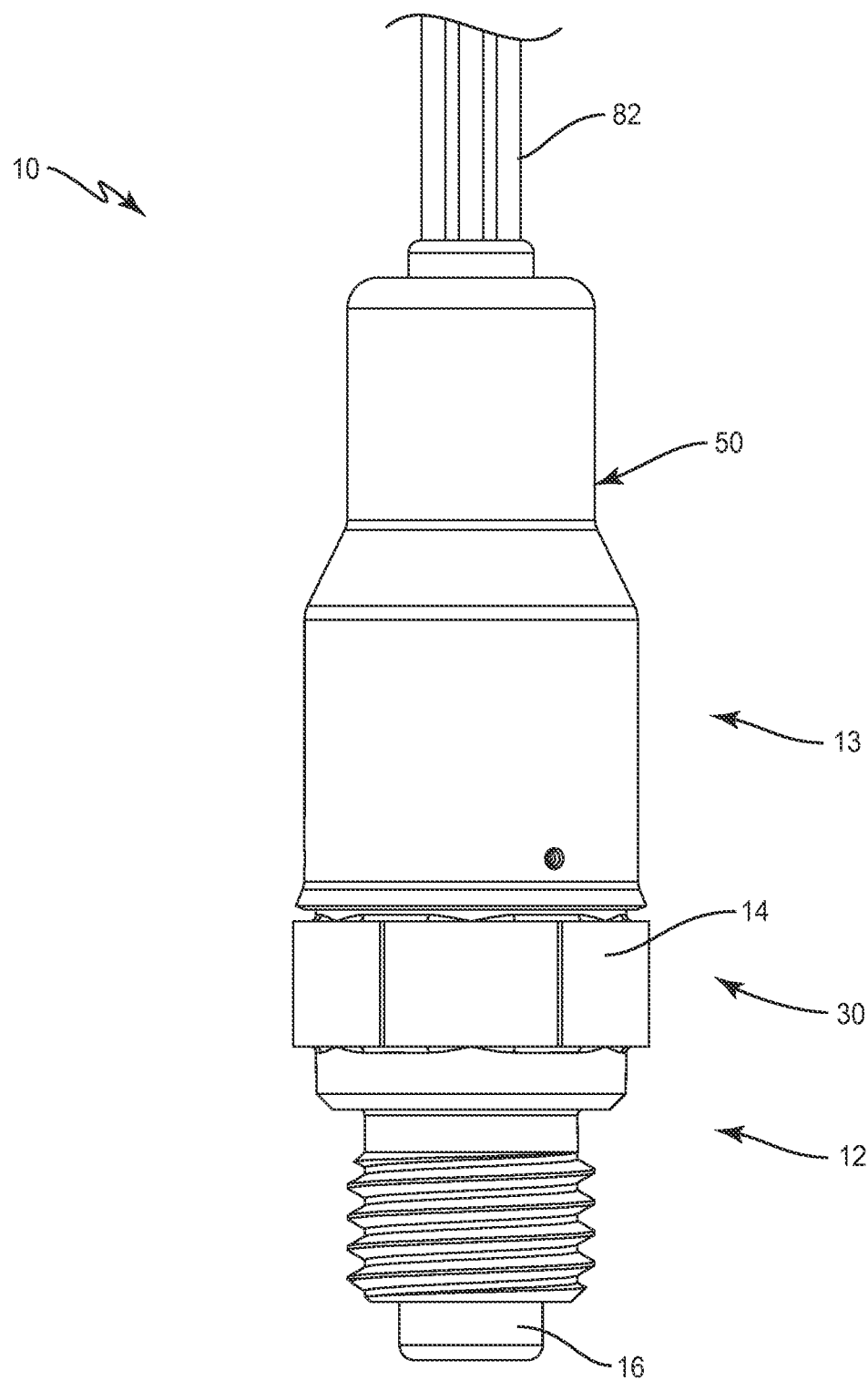
FIG. 1 shows an oxygen sensor assembly according to an embodiment of the present invention, with the cap portion mated to the base portion.
Figure 2:
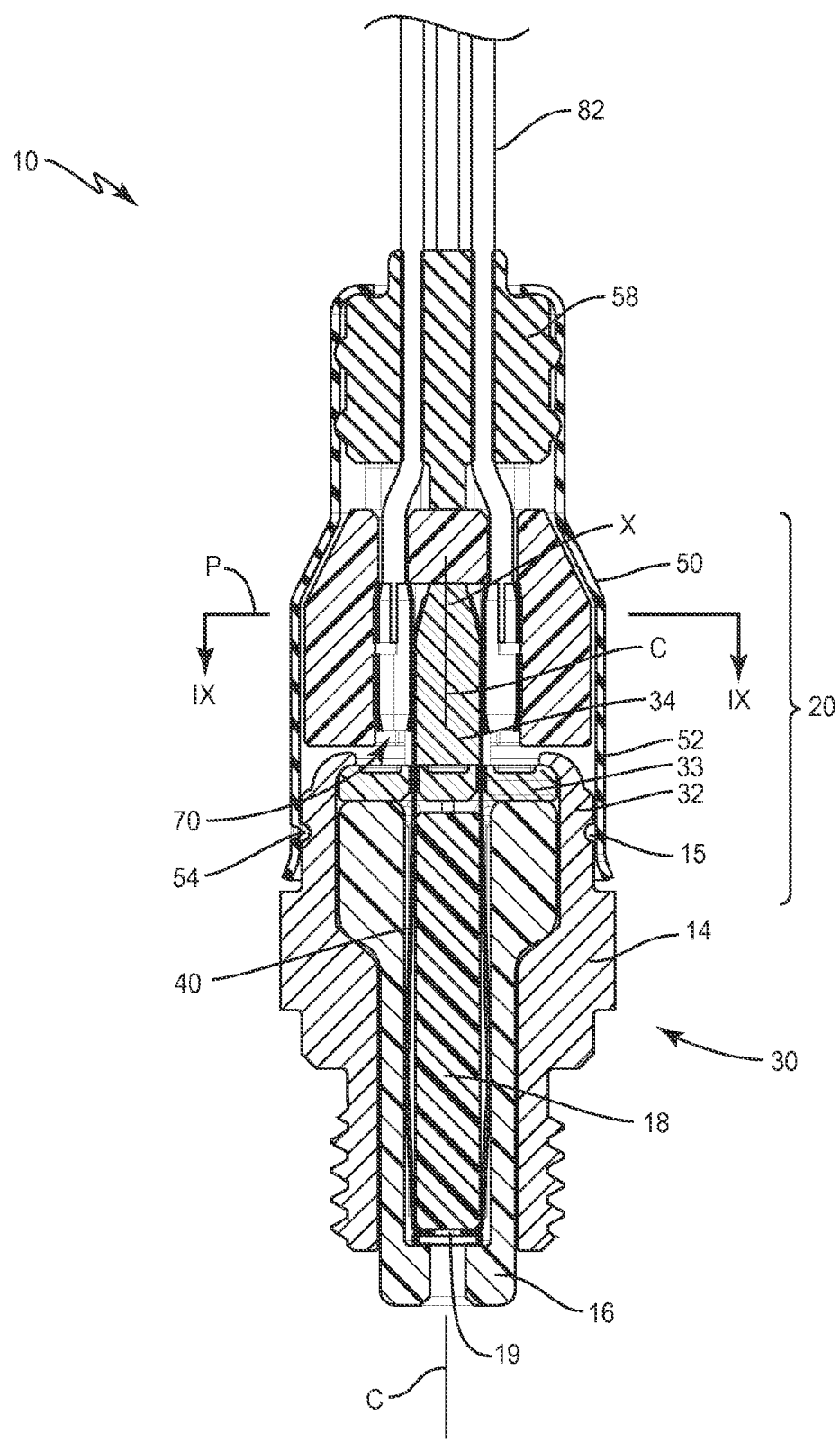
FIG. 2 shows a vertical cross-sectional view of the assembly of FIG. 1.

Referring to FIGS. 1-2, an exemplary oxygen sensor assembly, generally indicated at 10, includes a distal positioning section 12 and a proximal connection section 13. The distal positioning section 12 includes a mounting shell 14, typically externally threaded and in the form of a hexport housing, for mounting to a suitable location of an engine (not shown). A proximal portion of the mounting shell advantageously includes an external circumferential recess 15 for accepting detents 54, as discussed further below. A inner insulator 18 fits inside an outer insulator 16, which in turn fits inside the mounting shell 14. The outer insulator 16 includes an axial bore extending proximally from its distal tip. The inner insulator 18 supplies mounting support for an oxygen sensor chip 19 disposed distally from the tip of the inner insulator 18. A suitable oxygen sensor chip 19 is disclosed in U.S. Patent Application Publication No. 20110186446, the disclosure of which is incorporated herein in its entirety. The oxygen sensor chip 19 is exposed to the ambient environment via the bore of the outer insulator 16. The oxygen sensor chip 19 may advantageously be disposed in spaced relation to the tip of the inner insulator 18, and supported thusly by the distal portions of a plurality of flat conductor wires (or "leads") 40 bent as shown so as to clampingly hold the oxygen sensor chip 19. The inner insulator 18 and the outer insulator 16 are electrically insulating, and may be formed of suitable refractory or high temperature material. Thus, the leads 40 are electrically isolated from the typically conductive mounting shell 14.

Figure 3:
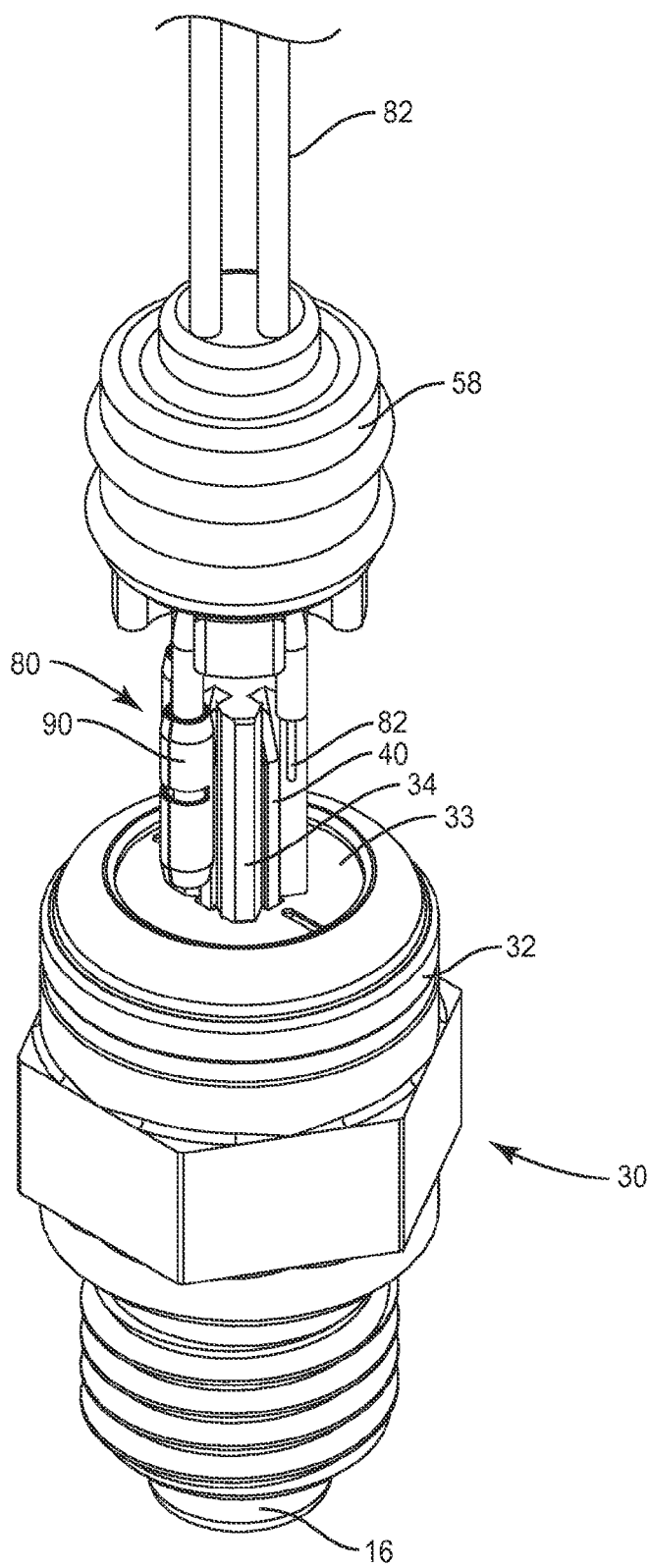
FIG. 3 shows a perspective view of the assembly of FIG. 1, with some elements of the cap portion omitted for clarity, including one spring omitted from the corresponding wire.
Figure 4:
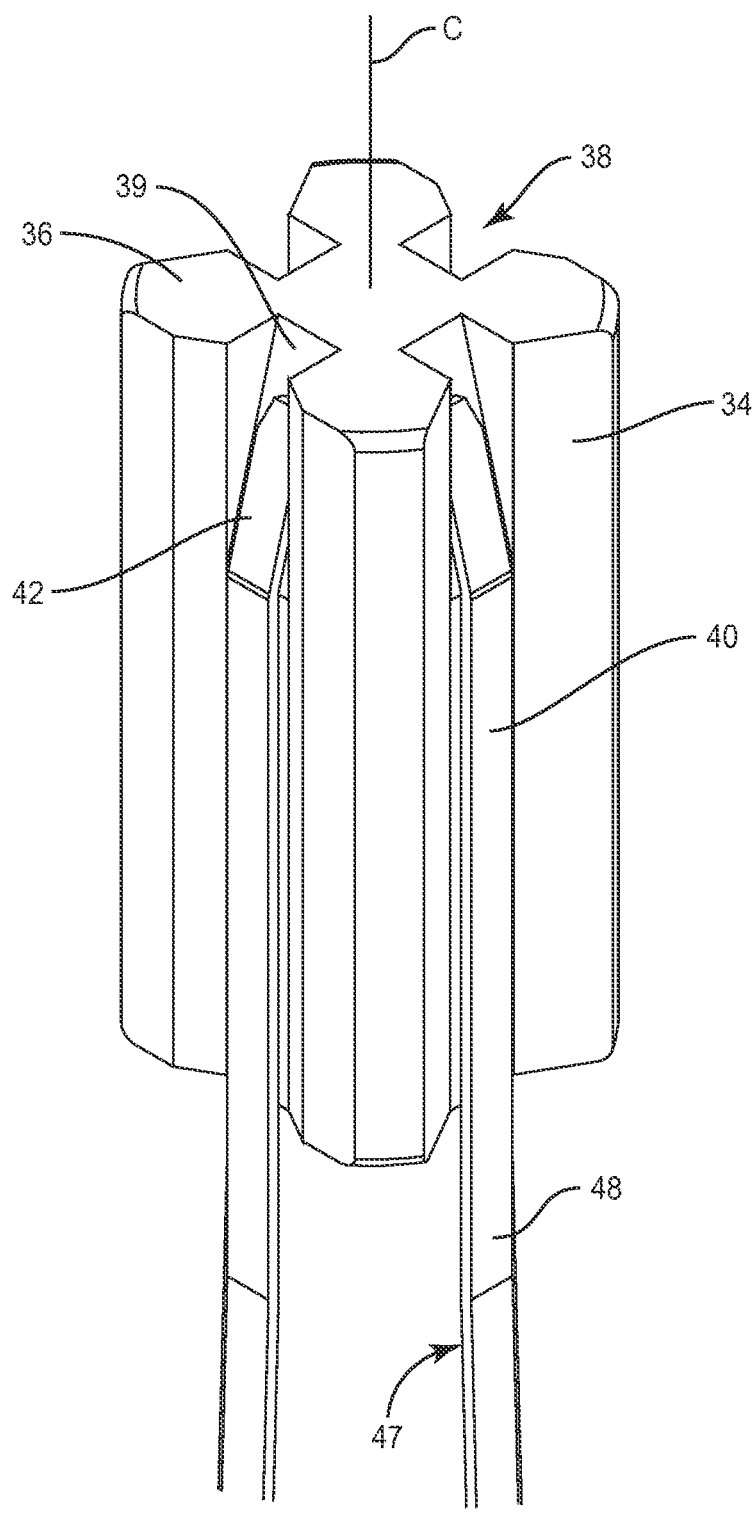
FIG. 4 shows a perspective view of a core, with two of four associated leads shown.
Figure 5:
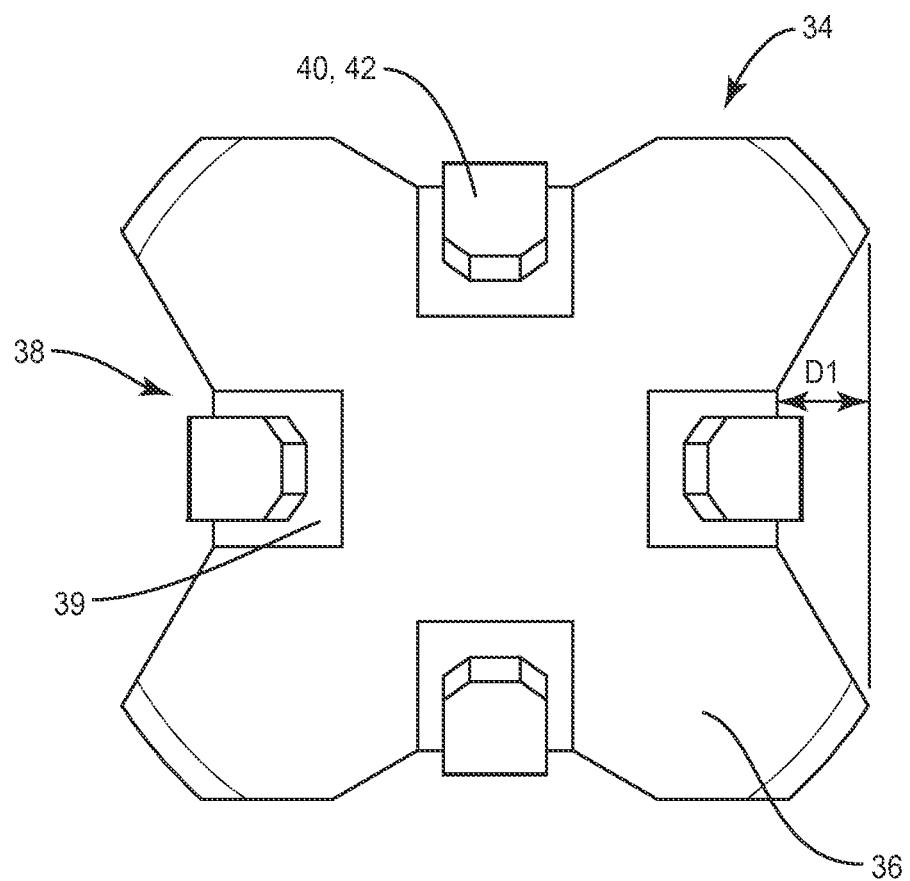
FIG. 5 shows a top view of the core of FIG. 4, with four associated leads shown.
Figure 6:
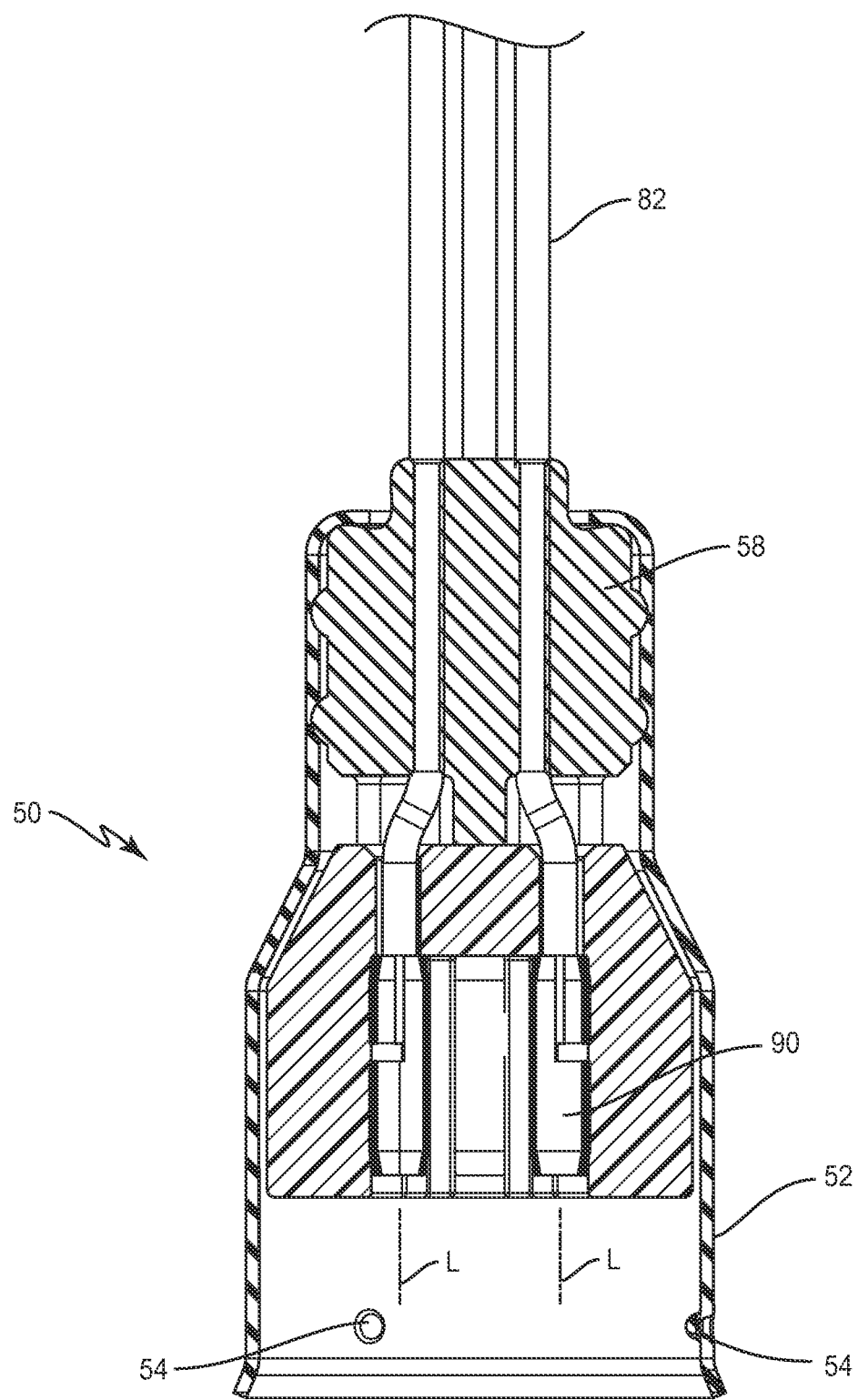
FIG. 6 shows a vertical cross-section of a cap portion.
Figure 7:
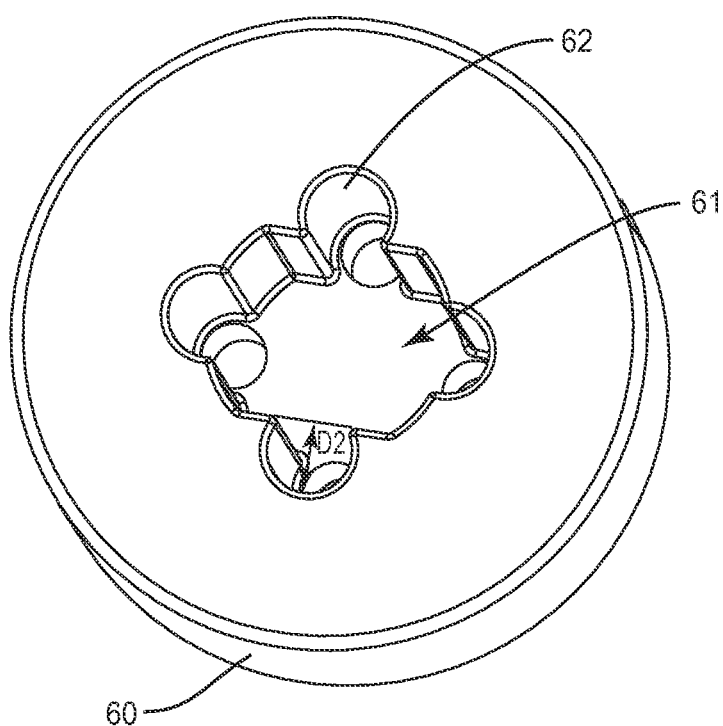
FIG. 7 shows a underside (distal) perspective view of a cap.

The connection section 13 is disposed proximally of the positioning section 12, and includes the connector assembly 20. The connector assembly 20 includes a base portion 30 and a cap portion 50 releasably mounted to the base portion 30. The base portion 30 is advantageously affixed to the positioning section 12 and includes a base 32 and a core 34 extending proximally from the base 32 along a core axis C. For the illustrative embodiment of FIGS. 2-3, the proximal portion (upper end portion as illustrated) of the mounting shell 14 and outer insulator 16 acts as the base 32. As shown in FIGS. 4-5, the core 34 advantageously includes a plurality of lobes 36, with recesses 38 formed therebetween that form channels 38 extending parallel to the core axis C. The channels 38 have a depth toward the core axis C, referred to as a radial depth, of D1. The core 34 is advantageously non-conductive and may be formed of a suitable material, such as a ceramic refractory material. Each lead 40 extends from the positioning section 12 and into the corresponding channel 38. While not required, the lead 40 may advantageously include a bent proximal section 42 that is bent inward toward the core axis C so that a portion of the lead 40 in the channel 38 extends in a direction transverse to the core axis C. The proximal end section of each channel 38 is advantageously ramped as shown at 39 to facilitate the connection process, as discussed further below. As can be appreciated, in the region of the channel 38, one lateral side 47 of the lead 40 directly faces the core 34 and the other lateral side 48 faces outward (toward the cap 60). Note that lateral side 47 may advantageously also abut the portion of the core 34 forming the "floor" of the corresponding channel 38.

Referring to FIG. 2 and FIGS. 6-9, the cap portion 50 includes an outer shell 52, an insulator cap 60, proximal conductor assemblies 80, and an optional proximal seal 58. The outer shell 52 helps protect the electrical connection formed by the connector assemblies 80 from the environmental contaminants. The outer shell 52 peripherally surrounds the cap 60, and includes a distal portion with one or more inner raised areas forming detents 54 for mating with the circumferential recess 15 of the mounting shell 14 to releasably hold the cap portion 50 to the base portion 30. The shell 52 may be conductive or non-conductive, as is desired. The insulator cap 60 resides inward of the shell 52 and helps electrically insulate the components therein from the shell 52. The cap 60 includes a plurality of longitudinally extending and distally opening recesses 62 that are advantageously generally part-round in cross-section. See FIG. 7. The recesses 62 are disposed in spaced relation to each other about a central longitudinally extending opening 61 which receives the core 34 as discussed further below. The opening 61 is distally open, and may be proximally closed or open as desired. Advantageously, the number of recesses 62 in the cap 60 match the number of channels 38 in the core 34 and are correspondingly positioned. The recesses 62 have a depth of D2. The combination of a given recess 62 in the cap 60 and the corresponding channel 38 in the core 34 both bound, and advantageously jointly form, a generally peripherally enclosed cavity 70 when the core 34 is inserted into the cap 60. Thus, the cavity 70 formed by a given recess 62 in the cap 60 and the corresponding channel 38 has a radial depth of D1+D2 in the portion thereof not including the ramped section 39 of the channel 38. Further, the cap 60 laterally bounds the cavity 70 in the outward direction. See FIG. 9. The cap 60 is non-conductive.

Figure 8:
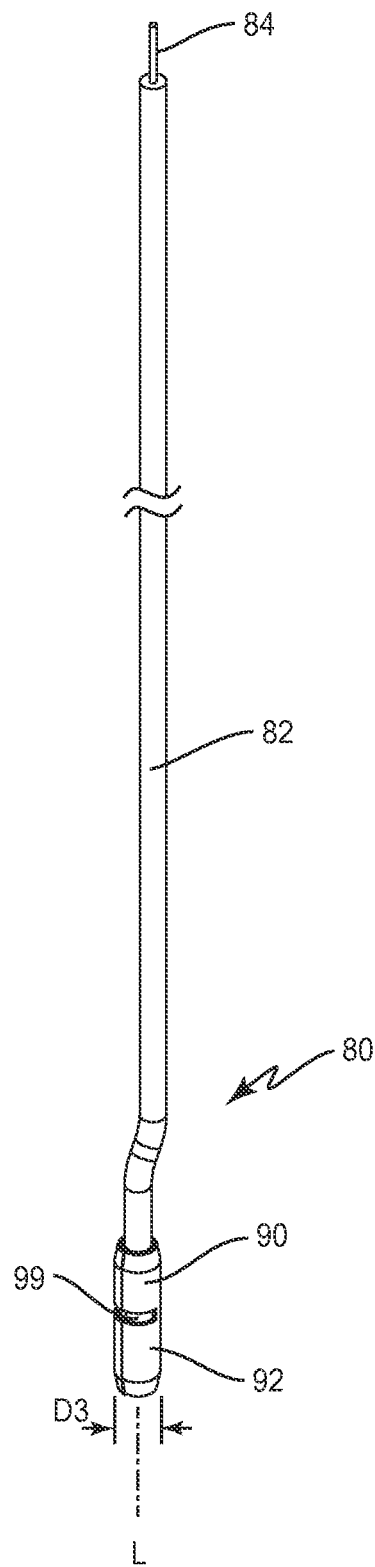
FIG. 8 shows one exemplary conductor assembly, of which there are four in the assembly of FIG. 1, with the spring laterally uncompressed.
Figure 9:
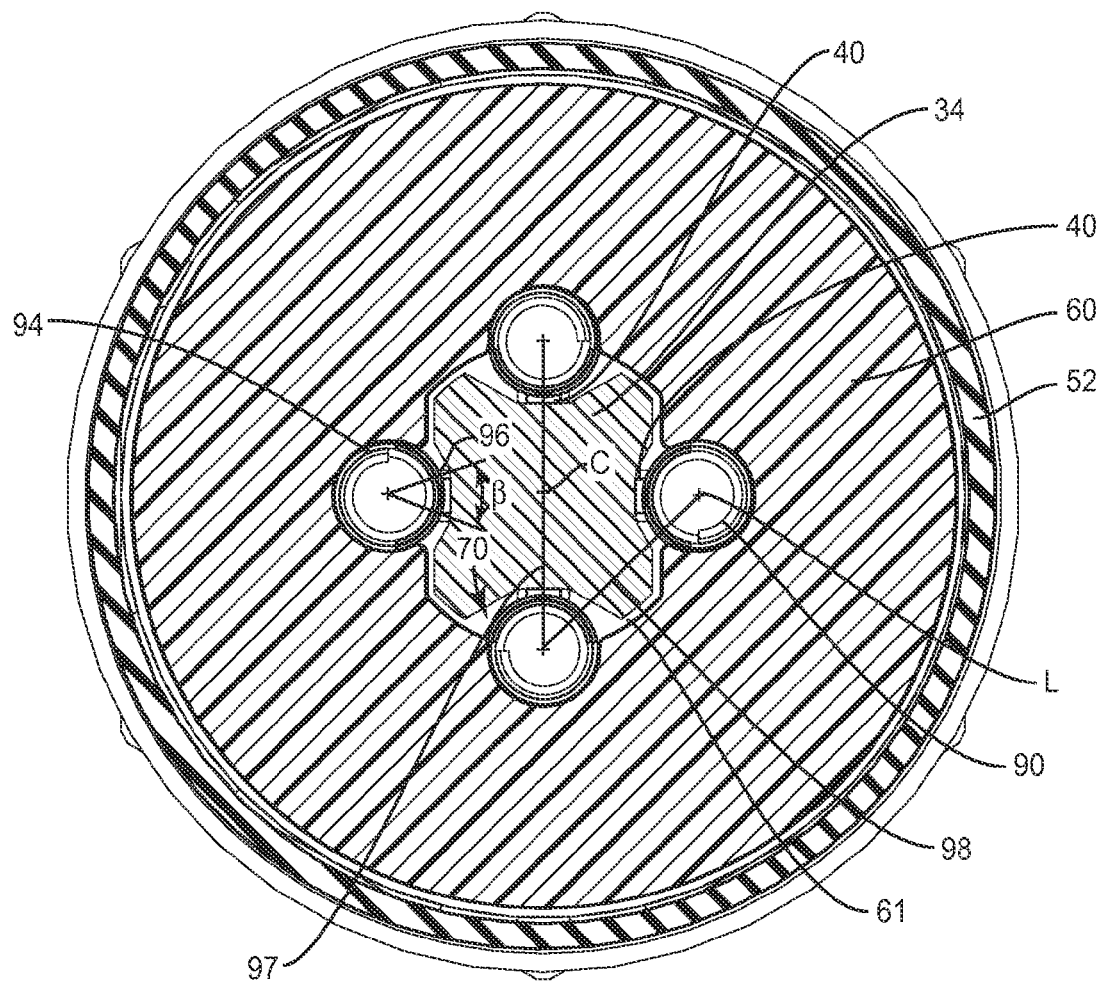
FIG. 9 shows a top cross-sectional view taken at plane P (see FIG. 2).

Referring to FIG. 8, the proximal conductor assemblies 80 each include a distal portion of a proximally extending wire 82, and a spring 90 mounted thereto at the distal portion. The wire 82 may take any suitable form known in the art, such as a plastically insulated conductive multi-stranded or solid copper conductor. The end portion 84 of the wire's conductor has the wire's insulation (if any) removed, and the spring 90 is mounted thereto. The spring 90 may be mounted to the wire 82 by any suitable means, such as by crimping, soldering, conductive epoxy, or a combination thereof. The spring 90 is resiliently laterally (radially) compressive with at least an electrically conductive outer surface. In some embodiments, the spring 90 may be a simple post-like generally cylindrical shell of spring material, or a solid but compressible pin. However, the spring 90 advantageously takes the form of a generally cylindrical body formed by a rolled convolute coil of resilient conductive material. An example of a suitable spring 90 is a coiled spring pin available from Spirol International Corporation of Danielson, Conn. The spring 90 extends longitudinally along a longitudinal spring axis L, which is advantageously parallel to the core axis C. The spring 90 includes a peripheral surface 92, part 94 of which is in contact with the cap 60, and another part 96 of which faces toward the core 34 of the base portion 30 and is in contact with the corresponding lead 40. See FIG. 9. The spring 90 has an uncompressed size (measured normal to the spring axis L) denoted D3. The distal tip of the spring 90 may be advantageously tapered inward toward the spring axis L, so as to have a smaller cross-sectional profile (measured normal to the spring axis L), to facilitate the mating of the cap portion 50 to the base portion 30.

The proximal seal 58 cooperates with the shell 52 so that debris, fluids, and other environmental contaminants are kept away from springs 90. The seal 58 may also aid in keeping the proximal conductor assemblies 80 properly aligned. The seal 58 is advantageously non-conductive.

As indicated above, the cap portion 50 is releasably attached to the base portion 30. When the cap portion 50 is disconnected from the base portion 30, the electrical connection between a given wire 82 and the corresponding lead 40, and hence the oxygen sensor chip 19, is opened. To make an electrical connection, the cap portion 50 is oriented relative to the base portion 30 such that the core axis C is parallel to the spring axes L, with the cap portion 50 spaced from the base portion 30. The cap portion 50 is then moved distally toward the base portion 30, along core axis C, so that the distal tips of the springs 90 begin to enter the corresponding recesses 38 on the core 34. The interaction of the ramped proximal end section 39 of the channel 38 and the tapered tip of the spring 90 facilitate entry of the spring 90 into the corresponding channel 38. The cap portion 50 is further distally advanced so that the detents 54 on the shell 52 engage the circumferential recess 15 of the mounting shell 14 to fully mate the cap portion 50 to the base portion 30. When fully mated, the cap portion 50 and the base portion 30 longitudinally overlap a significant extent. A portion of that overlap includes an area where a given spring 90 is pressed against its corresponding lead 40 so as to make the electrical connection. The pressing force is supplied, at least in part, by the lateral compression of the spring 90. Because the spring's uncompressed cross-sectional size D3 is larger than the lateral (radial) depth D1+D2 of the corresponding cavity 70, the spring 90 is laterally compressed when captured in the cavity 70 by mating the cap portion 50 to the base portion 30. This compression is facilitated by the convolute coil nature of the spring 90. That is, the individual layers of the spring 90 material making the coil are displaced relative to each other (e.g., the coil is "wound" tighter) so that the spring 90 is laterally compressed to reduce its cross-sectional size to match the available space, advantageously without changing its longitudinal length.

As can be appreciated, the spring 90 is laterally compressed between the lead 40 (backed by the core 34) and the cap 60 when the cap portion 50 is mated to the base portion 30. Thus, portion 94 of the outer peripheral surface 92 of the spring 90 abuts the cap 60, while portion 96 of the spring outer peripheral surface 92 abuts the lead 40, thereby making the electrical connection. This may be seen with reference to FIG. 9, which is a distally looking cross-section of the connector assembly 20 at plane P (at IX-IX in FIG. 2), which is normal the core axis C at location X along the core axis C. Location X is in the region of the spring 90, approximately longitudinally halfway along the zone where the spring 90 abuts the lead 40. As can be seen, peripheral surface portion 94 abutting the cap 60 is generally opposite the peripheral surface portion 96 that abuts the lead 40. The angle $\beta$ subtended by the conductor abutment portion 96 is advantageously not more than about three degrees to about ten degrees. Further, the conductor abutment portion 96 advantageously extends longitudinally for the majority of the longitudinal length of the spring 90, so that there is abundant area over which the electrical connection is made.

When the cap portion 50 is mated to the base portion 30, the electrical connection path formed in part by the connection assembly 20 extends along the proximally disposed wire 82, to the spring 90, to the lead 40 (conductor), and to the oxygen sensor chip 19, with the connection between the spring 90 and the lead 40 being releasable by unmating the cap portion 50 from the base portion 30. Note that the electrical connection between the spring 90 and the corresponding lead 40 is both readily releaseable and solderless.

As can be appreciated, the electrical connection may be readily made and released using the present approach. For example, the cap portion 50 may be releasably mated to the base portion 30, and the completed assembly used for a period of time. If a fault is subsequently detected in the oxygen sensor chip, or some other malfunction occurs, the cap portion 50 may be removed from the base portion 30, but remain "wired" to the engine control system. The base portion 30 may be dismounted from the engine and inspected for repair or replacement. For replacement, a different base portion 30 is then mounted to the engine and the original cap portion 50 is then mated to the new base portion 30. Of course, the sequence of mating/unmating the base portion 30 to the engine and the cap portion 50 may be reversed when appropriate. Thus, the oxygen sensor assembly 10 may be repaired/replaced without having to disconnect the cap portion 50 from the engine's control system.

The discussion above has been in the context of a connector assembly 20 making multiple parallel electrical connections. In one illustrative embodiment, there are four parallel connections, with pairs of springs 90 and leads 40 symmetrically disposed at 90° intervals around the core axis C. For such an arrangement, it may be advantageous to have opposing pairs of leads 40 form a circuit path through the oxygen sensor chip 19, the other pair of leads 40 forming a second and separate circuit path through the oxygen sensor chip 19. Further, for such an arrangement, a line 97 between the spring axes L of opposing springs 90 would pass through the core axis C, while a line 98 between spring axes L of adjacent springs 90 would pass through the core 34, but not the core axis C. Such an arrangement is believed advantageous; however, there may be more or less parallel connections, as is desired. Thus, there could be two, three, six, eight, etc. connections, which may be symmetrically or asymmetrically disposed. Further, the connector assembly 20 may make only one electrical connection (e.g., one spring 90 and one lead 40), as is desired. Additionally, if there is more than one lead 40 in a given recess 38, one spring 90 may make abutting electrical contact with more than one lead 40 in the base portion 30, such as might be advantageous for connecting a common ground.

The discussion above has generally assumed that the core 34 includes an appropriate number of channels 38 in which the corresponding leads 40 are partially disposed. Indeed, the illustrated core is symmetric about the core axis C. While such an arrangement is believed advantageous, such is not required. In some embodiments, the core 34 may have channels 38 that are asymmetrically disposed (with the recesses 62 advantageously being likewise asymmetrically disposed). Also, in some embodiments, the core 34 may not have channels 38, but instead have a flat and/or smooth exterior surface. Thus, the core 34 may, for example, have a rectangular, square, triangular, hexagonal, etc., or round cross-sectional profile, either with or without channels 38.

The core 34 and cap 60 may include suitable indexing features so as to help ensure that the cap 60 is properly aligned relative to the core 34 when the core is disposed in the core 60, so that the various leads 40 and conductors 82 are connected in a predetermined pattern, or a limited number of patterns. For example, the core 34 may have a generally rectangular cross-section, and the opening 61 in the cap 60 may have a corresponding rectangular shape, thereby allowing the core 34 to be inserted into the cap 60 in two possible orientations. Other indexing/keying features known in the art, such as key tabs/slots, may be used additional or alternatively.

While the description above has included one or more seals 58, more or less seals may be employed as appropriate to help keep environmental contaminants away from the electrical connection area. For example, the base portion 30 may include a seal 33 disposed between the core 34 and the inner insulator 18.

The discussion above has been in the context of the shell 52 of the cap portion 50 fitting over the proximal end of the base portion 30, so that the cap portion 50 encloses the proximal portion of the base portion 30 and forms the outermost portion of the assembly 20 where the cap portion 50 and the base portion 30 overlap. While this is believed to be advantageous, in some embodiments, the base portion 30 may have an outer rim wall (not shown) that the cap portion 50 is received into such that the base portion 30 is the outermost portion of the assembly 20 in the overlap region. Regardless of the shell configuration, because the core 34 fits into the cap 60 to form the electrical connection, the base portion 30 with the core 34 is considered the male portion of the connector assembly 20, while the cap portion 50 with the cap 60 is considered the female portion of the connector assembly 20.

In some embodiments, the spring 90 may have a notch 99 cut therethrough, generally perpendicular to the spring axis L, and advantageously oriented away from the core 34. Further, while it is believed advantageous if the leads 40 are formed by flat wires, the leads 40 may be formed by round, obround, or other shaped conductors, as is desired.

In some embodiments, a silicone-based thermoplastic or other suitable seal material can be applied to the circumferential recess 15 of mounting shell 14, which, upon heating, will flow into the space between the base 32 and the shell 52 in order to improve the sealing of the electrical connection from environmental elements like moisture, oils, other fluids, etc. This flowable seal material may require removal and replacement in subsequent re-connections; however, there may be advantages to using such flowable seal material in particularly harsh environments.

As mentioned above, the connection approach may be used for other applications than as a part of an oxygen sensor assembly 10. For example, a similar structure may be used, with a simple replacement of oxygen sensor chip 19 with a different sensor chip, such as a dedicated ignition spark detector, or other detector. Likewise, the connection approach could advantageously be used on other, non-combustion engine applications where it is desired to allow for repair/replacement with minimal or no rewiring.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A releasable electrical connector assembly, comprising:
   a cap portion releasably mated to a base portion such that the cap portion and the base portion longitudinally overlap;
   the cap portion comprising:
   an electrically non-conductive cap outwardly laterally bounding a cavity;
   a first electrical conductor assembly extending through the cap and partially disposed in the cavity; the first electrical conductor assembly comprising a first conductor and a spring mounted to a distal end portion of the first conductor; the spring extending along a longitudinal spring axis and having a circumference about the spring axis;
   the base portion comprising:
   a core extending proximally toward the cap;
   an electrically conductive lead disposed outward of the core;
   wherein the spring is laterally compressed between the cap and the lead such that, at a first longitudinal location along the spring axis, a first portion of the circumference of the spring is non-conductively abutting the cap and a second portion of the circumference, disposed at the first longitudinal location along the spring axis, is electrically conductively abutting the lead;
   wherein the lead, at the first location, directly faces the core on a side of the lead opposite the spring.

2. The releasable electrical connector assembly of claim 1, wherein the base portion is proximally enclosed by the cap.

3. The releasable electrical connector assembly of claim 1, wherein the spring comprises a coil having multiple layers disposed in convolute fashion about the spring axis.

4. The releasable electrical connector assembly of claim 1:
   wherein the lead is a first lead;
   wherein the electrically conductive wire is a first wire;
   wherein the spring is a first spring;

further comprising:
a second electrically conductive lead disposed outward of the core;
a second electrically conductive wire extending through the cap and having a second end portion disposed in the cavity;
a second spring mounted to the second end portion; the second spring extending along a second longitudinal spring axis and having a circumference about the second spring axis;
wherein the second spring is laterally compressed between the cap and the second lead such that a first portion of the circumference of the second spring is non-conductively abutting the cap and a second portion of the circumference of the second spring, disposed at a same longitudinal location along the spring axis as the first portion of the second spring, is electrically conductively abutting the second lead.

5. The releasable electrical connector assembly of claim 4 wherein the first and second spring axes are disposed symmetrically relative to the core.

6. The releasable electrical connector assembly of claim 1 wherein second portion of the circumference subtends an angle of not more than about 10° about the spring axis.

7. The releasable electrical connector assembly of claim 1 wherein the base portion further comprises an oxygen sensor electrically coupled to the lead.

8. A releasable electrical connector assembly, comprising:
a female cap portion releasably mated to a male base portion such that the cap portion and the base portion longitudinally overlap;
the female cap portion comprising:
an electrically non-conductive cap outwardly laterally bounding a first cavity;
a first electrical conductor assembly extending through the cap and having an distal end portion disposed in the cavity; the first electrical conductor assembly comprising a first conductor and a first spring mounted to a distal end portion of the first conductor; the spring extending distally along a longitudinal first spring axis and having a circumference about the first spring axis;
the male base portion comprising:
a nonconductive core extending proximally toward the cap along a longitudinal core axis and having an outer surface disposed about the core axis;
a first electrically conductive lead disposed outward of the outer surface of the core;
wherein the core and the first lead are disposed in the cap so that:
proximate the cavity, the first lead is pressed between the outer surface of the core and the first spring;
the spring is laterally compressed normal to the first spring axis between the first lead and the cap;
an electrical path extends between the first conductor and the first lead via the first spring.

9. The releasable electrical connector assembly of claim 8:
wherein the cap further outwardly laterally bounds a second cavity that is spaced from the first cavity about the core axis;
wherein the female cap portion further comprises a second electrical conductor assembly extending through the cap and partially disposed in the second cavity; the second electrical conductor assembly comprising a second conductor and a second spring mounted to a distal end portion of the second conductor; the second spring extending distally along a longitudinal second spring axis and having a circumference about the second spring axis;
wherein the male base portion further comprises a second electrically conductive lead disposed outward of the outer surface of the core in spaced relation to the first lead;
wherein the core and the second lead are disposed in the cap so that:
the second lead is pressed between the outer surface of the core and the second spring;
the second spring is laterally compressed normal to the second spring axis between the second lead and the cap;
an electrical path extends between the second conductor and the second lead via the second spring.

10. The releasable electrical connector assembly of claim 9 wherein the first and second springs, and the first and second leads, are disposed symmetrically relative to the core axis.

11. The releasable electrical connector assembly of claim 9 wherein a theoretical line between the first spring axis and the second spring axis passes through the core without passing through the core axis.

12. A method of electrical connection, the method comprising:
providing a cap portion comprising:
an electrically non-conductive cap bounding a cavity;
a first electrical conductor assembly extending through the cap and having an end portion disposed in the cavity; the first electrical conductor assembly comprising a first conductor and a spring mounted to a distal end portion of the first conductor; the spring extending along a longitudinal spring axis and having a peripheral external surface disposed about circumferentially surrounding the spring axis;
providing a base portion distinct from the cap portion and comprising:
a core extending proximally along a longitudinal base axis toward the cap;
an electrically conductive lead disposed outward of the core;
moving the cap portion distally and relative to the base portion and to engagement therewith so as to releasably mate the cap portion to the base portion such that the cap portion and the base portion longitudinally overlap;
wherein the releasably mating causes lateral compression of the spring between the cap and the lead such that a first portion of the external surface of the spring non-conductively abuts the cap and a second portion of the external surface, disposed at a same longitudinal location along the spring axis as the first portion, electrically conductively abuts the lead to electrically connect the first conductor to the lead.

13. The method of claim 12 wherein the releasably mating comprises proximally enclosing the base portion with the cap portion.

14. The method of claim 12 further comprising crimping the spring to the end portion of the first conductor.

15. The method of claim 12 wherein the cap portion further comprises a shell disposed outwardly from the cap, wherein the releasably mating comprises releasably engaging the shell with the base portion.

16. The method of claim 12:
wherein the base portion is a first base portion and the lead is a first lead;
further comprising providing a second base portion comprising:

a second core extending proximally along a longitudinal second base axis;
a second electrically conductive lead disposed outwardly from the second core;
further comprising removing the first base portion from the cap portion so as to break an electrical connection between the first conductor and the first lead;
thereafter, releasably coupling the cap portion to the second base portion such that the cap portion and the second base portion longitudinally overlap;
wherein the releasably coupling the cap portion to the second base portion causes lateral compression of the spring between the cap and the second lead such that a third portion of the external surface of the spring nonconductively abuts the cap and a fourth portion of the external surface, disposed at a same longitudinal location along the spring axis as the third portion, electrically conductively abuts the second lead to electrically connect the first conductor to the second lead.

17. The method of claim 16 wherein the first and third portions of the external surface of the spring are the same.

18. The method of claim 12 wherein the releasably mating comprises releasably mating via a detent.

19. The method of claim 12:
wherein the core includes a longitudinal channel;
wherein the releasably mating comprises disposing a portion of the external surface of spring in the channel.

20. A method of electrical connection, the method comprising:
releasably mating a female cap portion to a male base portion such that the cap portion and the base portion longitudinally overlap;
wherein the female cap portion comprises:
an electrically non-conductive cap having a cavity;
a first electrical conductor assembly extending through the cap and having an distal end portion disposed in the cavity; the first electrical conductor assembly comprising a first conductor and a first spring mounted to a distal end portion of the first conductor; the spring extending distally along a longitudinal first spring axis and having a circumference about the spring axis;
wherein the male base portion comprises:
a nonconductive core extending proximally toward the cap along a longitudinal core axis and having an outer surface disposed about the core axis;
a first electrically conductive lead disposed outward of the outer surface of the core;
wherein the mating comprises moving the female cap portion distally toward the male base portion such that:
the core enters an opening of the female cap;
the first lead is pressed inward between the outer surface of the core and the first spring;
the spring is laterally compressed normal to the first spring axis between the first lead and the cap;
an electrical path is formed between the first conductor and the first lead via the first spring.

* * * * *